Sept. 6, 1955 E. W. PAWLA Plant Pat. 1,418
VIOLA PLANT
Filed Sept. 7, 1954
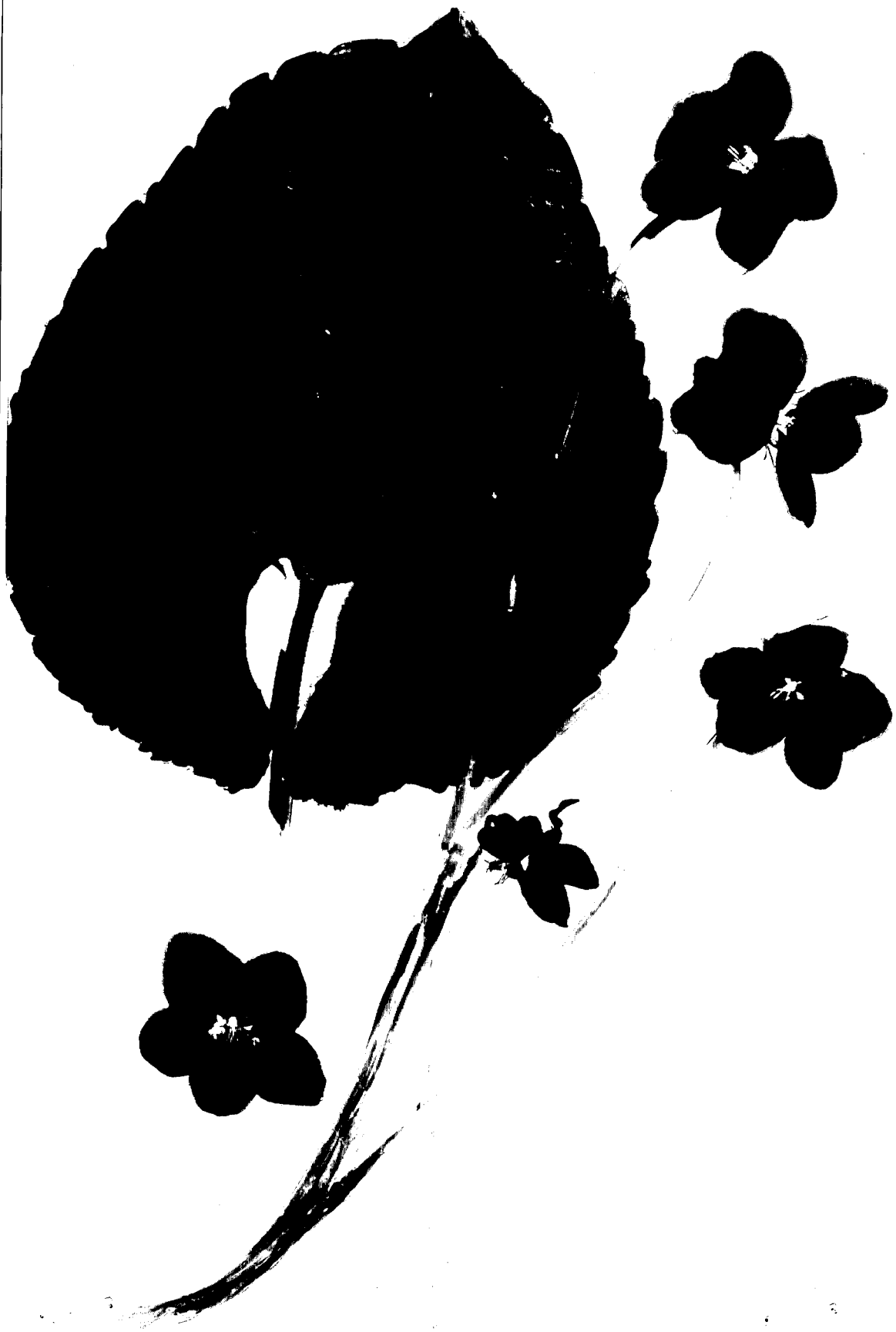

United States Patent Office

Plant Pat. 1,418
Patented Sept. 6, 1955

1,418

VIOLA PLANT

Edith Wintermute Pawla, Capitola, Calif.

Application September 7, 1954, Serial No. 454,648

1 Claim. (Cl. 47—60)

The present invention relates to a new and distinct variety of viola plant, originated by the crossing of two varieties, the "Royal Elk" and the "Pansy Violet, unpatented."

This new variety has the outstanding characteristics of giant size of bloom and plant together with decided perfume, unusually long stems of from 8 to 12 inches which stand firmly erect.

This new variety has greater commercial value for cut blooms because of the unusual size; blossoms measure from 1½ to 2½ inches across, which is most unusual for violets. They have a distinctive fragrance. The long erect stems also increase their value for flower arrangements, corsages, and general garden planting.

In addition to the size and beauty of the blooms, the plant has a long sturdy root structure. It is resistant to both dryness and frost.

The new variety was observed in the Pawla Violet Gardens at Capitola, California, in January 10, 1948. These plants are now being grown through asexual reproduction (root cuttings) in the above mentioned gardens. The described characteristics hold true through many succeeding propagations.

Following is a detailed description of this new variety: (Color plates referred to are from "Dictionary of Color" by Moerz & Paul.)

Classification: Botanic *Viola odorata.*

Parentage: Seed parent, Royal Elk; pollen parent, Pansy Violet.

Flower: Large—size from 1½ to 2½ inches across length or width.

Petalage: Five rounded petals, two upper, two lateral, one lower. Very little appearance of separation of petals as they tend to a generally circular outer contour. Beards and peacock coloring on the two lateral petals.

Spur: Very sort and slightly rounded.

Sepals: Five—color green.

Pistil: Orange.

Fragrance: True sweet violet.

Texture: Petals volutinous.

Color: Violet (Plate 42, page 107, line 12).

Stems: Length 8 to 12 inches. Has a somewhat fibrous core that assists in holding the bloom erect, not limp, as with most varieties. Stems snap easily from base, making picking easier.

Blooming habit: From September to May (in California). Blooms last about ten days. Recurrent.

Propagation: By sections, cuttings, or stolons which root readily.

Roots: The roots reach a depth of from 7 to 14 inches, making the plant more resistant to frost or dryness. With proper care they produce a most vigorous growth so that plants at maturity cover 18 to 30 inches.

Foliage: Foliage and flowers arise in clusters from stolons branching laterally above the ground.

Size: Five to eight inches across.

Shape: Slightly pointed tip terminates the heart shaped slightly serrated leaf. Base lobes extend so as to overlap beyond the base of the stem.

Texture: Heavy, thick, deep veined.

Color leaf: Light green back. (Plate 24, page 71, L–1.) Face of leaf: (Plate 16, page 55, J–1).

Petiole: Length 8 to 14 inches—stand firm and erect.

Fragrance: At certain seasons the leaves have a violet scent.

I claim:

A new and distinct variety of viola plant substantially as herein described and illustrated, characterized by large fragrant blooms on unusually long stems, with a root structure which has a habit of rooting by thick lateral stolons, roots reaching a great depth making the plant highly resistant to dryness and frost.

No references cited.